United States Patent [19]

Stunberg

[11] Patent Number: 5,335,257
[45] Date of Patent: Aug. 2, 1994

[54] METHOD AND APPARATUS FOR CONTROLLING THE COMPRESSION FORCE IN X-RAY EQUIPMENT FOR MAMMOGRAPHIC EXAMINATIONS

[75] Inventor: Stefan Stunberg, Stockholm, Sweden

[73] Assignee: Siemens Elema AB, Solna, Sweden

[21] Appl. No.: 43,807

[22] Filed: Apr. 7, 1993

[30] Foreign Application Priority Data

Apr. 10, 1992 [SE] Sweden .............................. 92011576

[51] Int. Cl.5 .............................................. H05G 1/30
[52] U.S. Cl. ........................................ 378/37; 378/95; 378/117
[58] Field of Search ................ 378/37, 95, 114, 117, 378/208, 195

[56] References Cited

U.S. PATENT DOCUMENTS

| | | |
|---|---|---|
| 3,971,950 | 7/1976 | Evans et al. . |
| 3,991,316 | 11/1976 | Schmidt et al. . |
| 4,090,084 | 5/1978 | Epstein et al. ............ 378/37 |
| 4,658,409 | 4/1987 | Summ . |
| 4,744,099 | 5/1988 | Huettenrausch et al. . |

FOREIGN PATENT DOCUMENTS

| | | |
|---|---|---|
| 0435837 | 11/1990 | European Pat. Off. . |
| 1942490 | 8/1974 | Fed. Rep. of Germany . |
| 8701555 | 3/1987 | PCT Int'l Appl. ............ 378/37 |

*Primary Examiner*—David P. Porta
*Attorney, Agent, or Firm*—Hill, Steadman & Simpson

[57] ABSTRACT

In mammographic examinations, the breast being examined is compressed with increasing force between a pressure plate and a support platform. A method and apparatus are disclosed for generating an optimal compression pressure which is adapted to the size of the breast being examined, so as to insure reliably high image quality. In the method and apparatus, the compression pressure of the pressure plate against the breast is controlled so that the increase in compression force is stopped when a change in breast thickness reaches a predetermined value. The apparatus includes a measuring device for establishing the distance between the pressure plate and the support platform, thereby establishing the thickness of the breast as the compression force increases, and a control device which stops the increase in the force of compression when the change in this distance reaches a predetermined value.

10 Claims, 3 Drawing Sheets

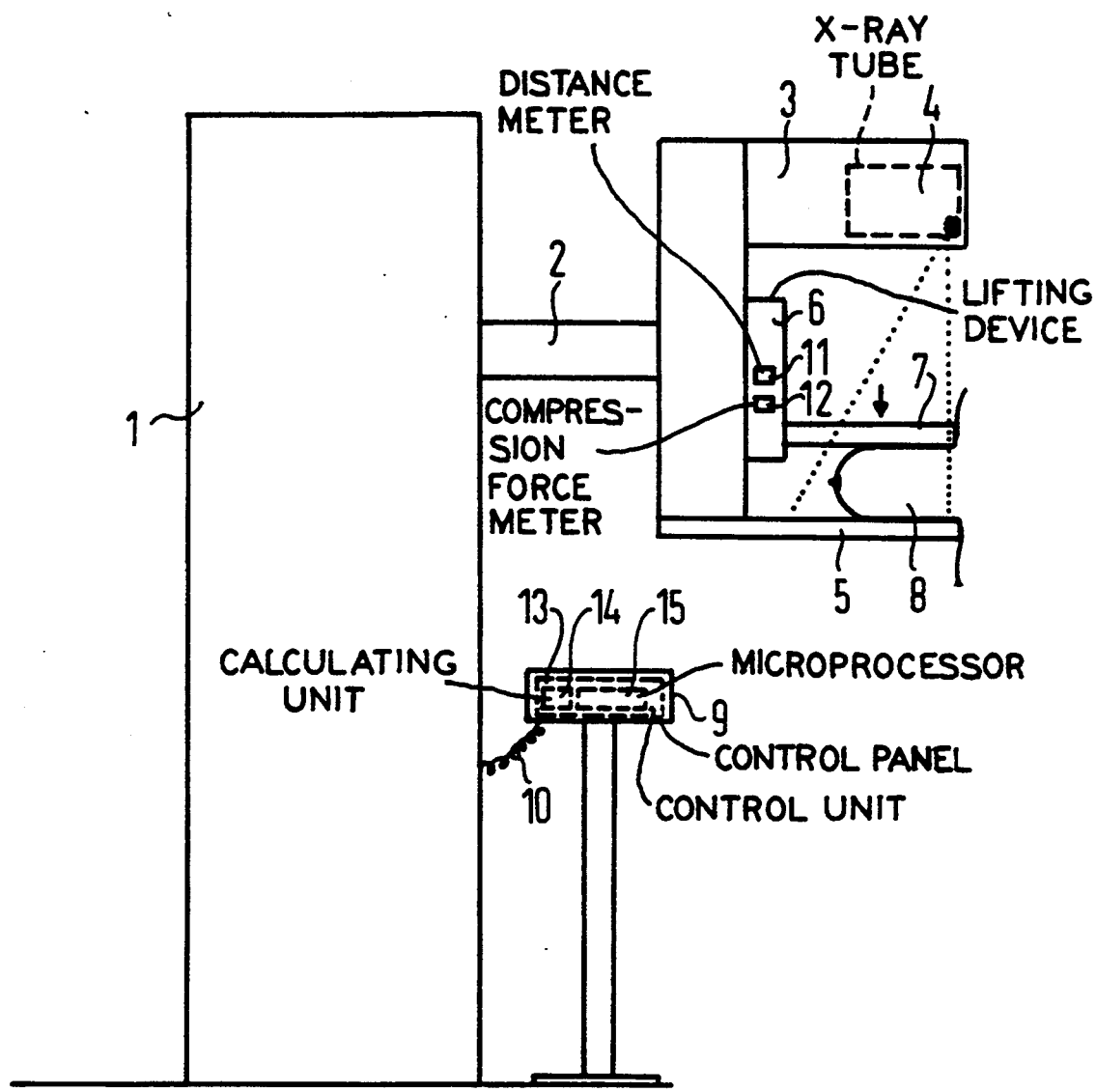

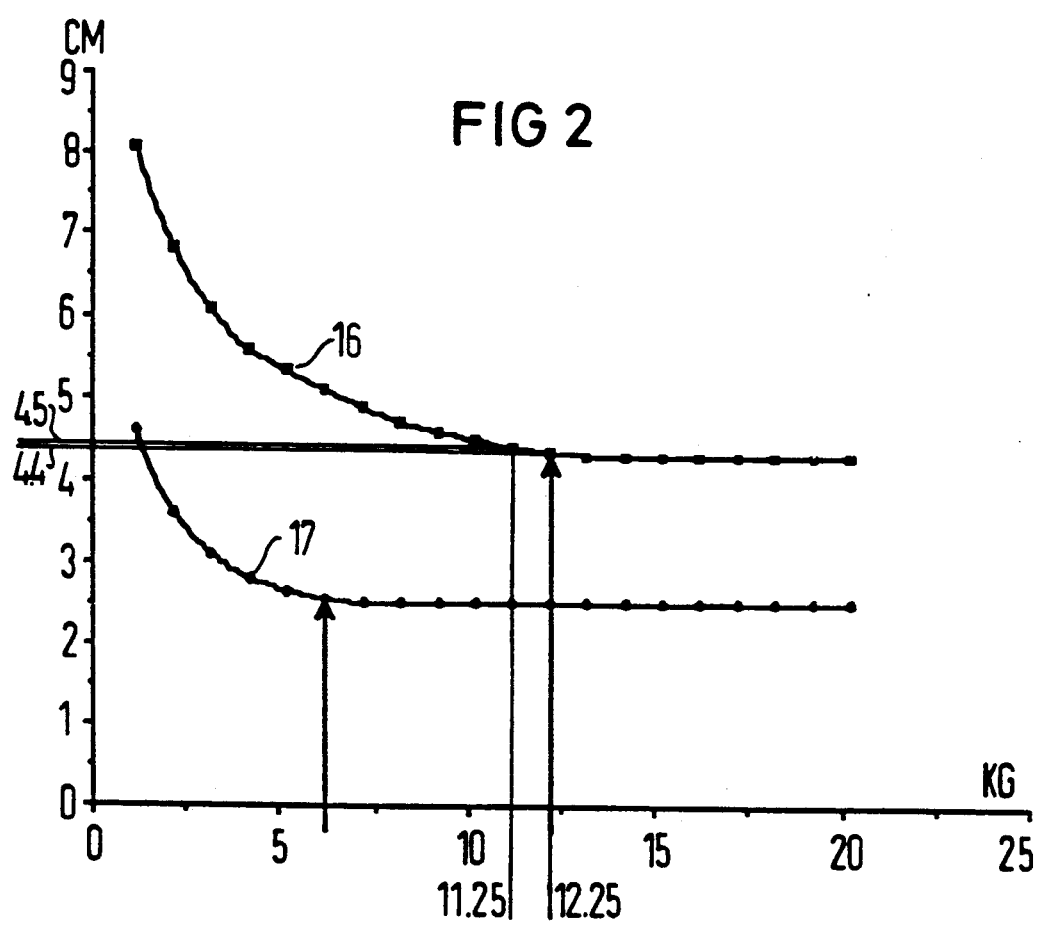

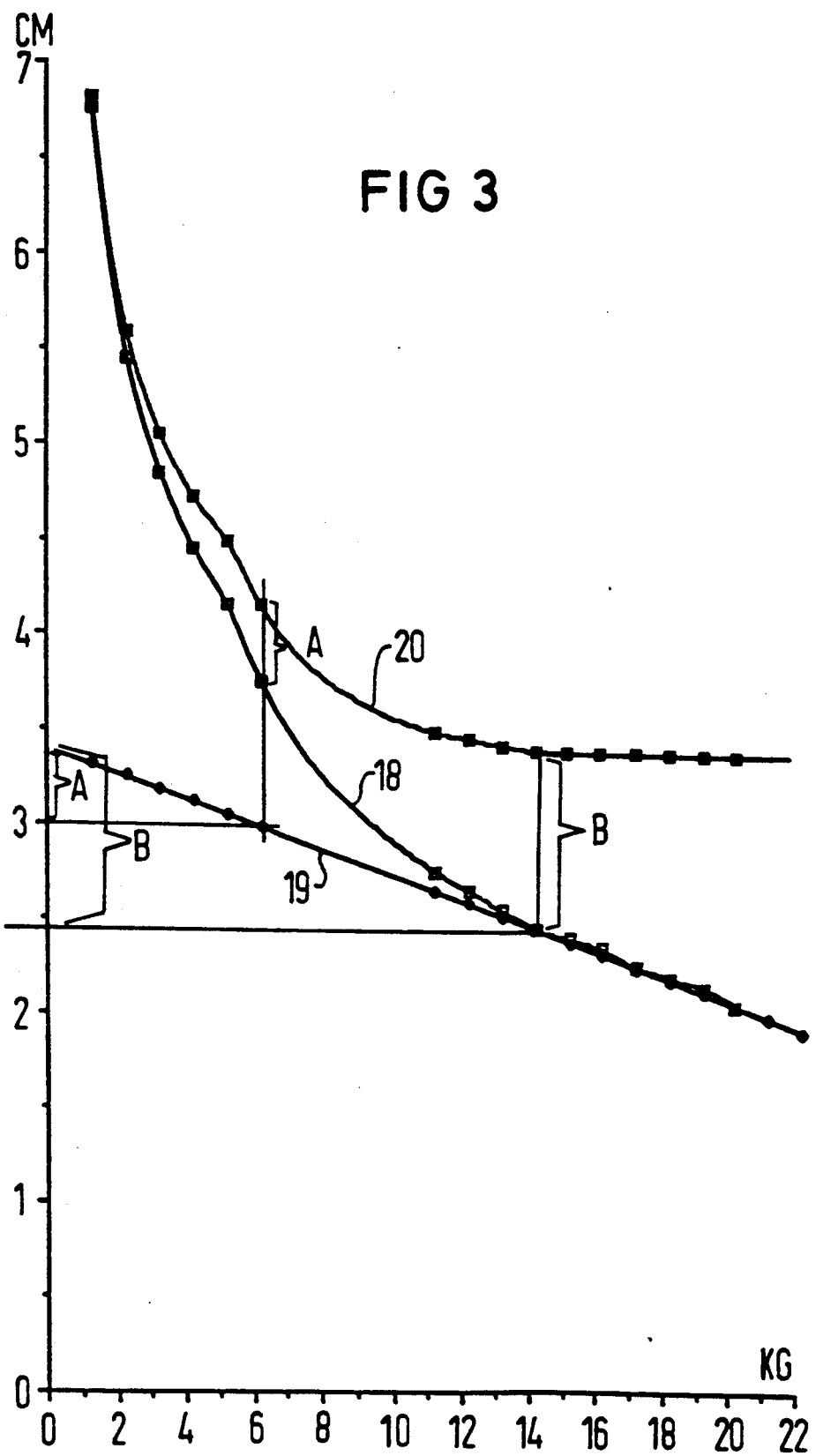

METHOD AND APPARATUS FOR CONTROLLING THE COMPRESSION FORCE IN X-RAY EQUIPMENT FOR MAMMOGRAPHIC EXAMINATIONS

BACKGROUND OF THE INVENTION

1. Field of the Invention

The present invention is directed to a method and apparatus for controlling the compression force in an x-ray apparatus for mammographic examinations, of the type wherein a breast under examination is compressed with increasing force between a pressure plate and a support platform.

2. Description of the Prior Art

For good image quality in radiographic examinations of a breast, it is known that optimal compression of the breast is necessary to minimize the amount of secondary radiation from breast tissue. Such secondary radiation impairs image quality, and decreases with decreasing breast thickness.

A known procedure for compressing a breast under examination is described European Application 0 435 837 wherein the compression force increases as the pressure plate is advanced at a uniform speed to a preset position, with the pressure plate thereafter being advanced at a decreasing speed until a predetermined, non-variable end value of the compression force is reached. A disadvantage of this procedure is that the preset end value is not adapted to all breast sizes, and can therefore result in a compression force, exerted by the plate against the breast, which is too large or too small. In the case of a small breast, the patient may experience pain caused by excessive compression of the breast, but the compression force may not be large enough to generate a satisfactory image quality with a large breast.

SUMMARY OF THE INVENTION

It is an object of the present invention to provide a procedure for controlling the compression force in an x-ray apparatus wherein optimal compression pressure is generated which is adapted to each patient's breast size, so that high image quality is always assured, and pain to the patient is avoided.

It is a further object of the present invention to provide an apparatus operating in accordance with such a procedure. The above objects are achieved in a method and apparatus wherein the compression force exerted by the pressure plate against the breast is governed by the breast thickness such that the increase in compression force is stopped when the change in the breast thickness reaches a preset value. The compression force is controlled by taking variations in breast thickness into account as the breast is compressed, so that the increase in compression pressure is stopped when the thickness of the compressed breast exhibits no further appreciable change. In this manner, a breast is never subjected to needlessly high or low compression pressure, and a high quality radiograph can always be obtained.

In a further embodiment of the method, the increase in the compression force is stopped when the change in breast thickness, related to the change in compression force, reaches a predetermined value. This predetermined value is preferably zero.

In the apparatus for practicing the method, first means are provided for determining the distance between the pressure plate and the support platform, and thus for establishing the thickness of the breast as the compression force increases. A control device stops the increase in the compression force when the change in the measured distance reaches a preset value. In this manner, optimal compression force is applied to the breast in a simple manner, regardless of the thickness of the breast, resulting in the above-described advantages.

In a further embodiment of the apparatus, the pressure plate is flexible, and is bent in a defined manner with increasing compression force. The distance between the pressure plate and the platform table, as measured by the firs means, can then be corrected with a value to compensate for pressure plate bending. The pressure plate is bent with increasing compression force in such a manner that the distance between its free end and the support platform becomes greater than the distance between the attached end of the pressure plate and the support platform. The correction value compensates for the difference between these two distances.

In a preferred embodiment of the invention, the apparatus includes second means for measuring compression force, with the measurement value from this second measuring means, plus the distance value obtained by the first measuring means, being sent to a means for calculating the current rate of change of the distance with respect to the current rate of change of the compression force, and the ratio is compared to the aforementioned preset value. The control device stops the increase in the compression force when this ratio reaches the predetermined value.

The second means for measuring compression force and the first means for measuring the distance are preferably disposed in the lifting device which operates the pressure plate. Disposing these measuring means close to the pressure plate is advantageous.

In a further embodiment of the invention, the values for the distance and the compression force can be sampled and sent to a microprocessor provided in the control device. The microprocessor calculates the aforementioned ratio, and may take the pressure plate bending into account as noted above, and compares the ratio to a reference value corresponding to the preset value. A control signal is then generated which stops the increase in compression force when the ratio reaches the preset value.

DESCRIPTION OF THE DRAWINGS

FIG. 1 is a side schematic view of an x-ray apparatus for mammographic examinations constructed in accordance with the principles of the present invention.

FIGS. 2 and 3 are diagrams respectively illustrating pressure plate movements in relation to the support platform and breast thickness as a function of the compression force.

DESCRIPTION OF THE PREFERRED EMBODIMENTS

An x-ray apparatus for mammographic examinations constructed in accordance with the principles of the present invention is shown in FIG. 1. The apparatus includes a stand 1 with a hood 3 carried by a shaft 2, the hood 3 containing an x-ray tube 4. A support platform 5 is attached to the hood 3, the support platform 5 also containing a cassette for x-ray film (not shown). A vertically moving lifting device 6 for the pressure plate 7 is also attached to the hood 3, to compress a breast 8. The movement of the pressure plate 7 can be controlled, for example, from a control panel 9 connected to the x-ray apparatus by a cable 10. Such control is undertaken with the assistance of measuring elements 11 and 12 in the lifting device 6. The measuring elements 11 and 12 respectively measure the compression force and the distance between the pressure plate 7 and the support platform 5, the latter measurement establishing the thickness of the compressed breast 8. The measurement element 11 may thus consist of a distance meter, and the measurement element 12 may be a compression force meter. The elements 11 and 12 are connected to a control device 13 in the control panel 9. Prior to exposure of a breast 8 placed on the support platform 5, the pressure plate 7 presses the breast 8 against the support platform 5. The increase in compression force is stopped when the change in the thickness of the breast 8, as measured by the distance meter 11, related to the change in the compression force, as measured by the compression force meter 12, reaches a predetermined value, for example zero.

The measurements obtained from the distance meter 11 and the compression force meter 12 are supplied continuously, or at short intervals, to a calculating unit 14 in the control device 13, which determines the ratio of the change in the distance between the compression plate 7 and the support platform 5 ($\Delta a$) with respect to the change in the compression force ($\Delta b$), resulting in a ratio $\Delta a/\Delta b$ as described in FIGS. 2 and 3. The control device 13 also includes a comparator 15, which compares the aforementioned ratio to a reference value corresponding to the predetermined value, which is preferably zero. A control signal is generated and supplied to the lifting device 6 for the pressure plate 7 when the ratio reaches the reference value, thereby stopping the increase in compression force. The calculating unit 14 and the comparator 15 may incorporated in a microprocessor.

FIG. 2 shows a diagram with a coordinate system in which the horizontal axis designates the compression force in kg, and the vertical axis designates breast thickness in cm. The curve 16 at the top of FIG. 2 illustrates the compression of a breast having a thickness of approximately 8 cm. when the compression force is about 2 kg. Measurement signals from the distance meter 11 and the compression force meter 12 are supplied to the aforementioned control device 13. When the rate of change of the curve 16, corresponding to the aforementioned ratio, reaches the predetermined value, the increase in compression force is stopped. In the embodiment shown in FIG. 2, this occurs, for example, when the distance between the pressure plate 7 and the support platform 6, i.e., the breast thickness, decreases only by approximately 1 mm. at an increase in compression force of about 1 kg. The compression force applied to the breast thus stops at about 12.25 kg. The curve 16 shows a negligible reduction in breast thickness if the compression force were to continue to increase. Any such increase in compression would only cause the pain to the patient, and would fail to produce any improvement in image quality. The curve 17 shows compression of a comparatively small breast, having a thickness of approximately 4.5 cm. when compression force is about 2 kg. In this instance, the aforementioned procedure stops the increase in the compression force at about 6 kg. The curve 17 also shows that the breast thickness is not appreciably reduced if the compression pressure were to increase. FIG. 2 clearly shows the difference in the end of the optimum compression force with respect to different breast thicknesses, and also demonstrates that the use of a predetermined fixed end value for the compression force, without regard to breast thickness, is merely arbitrary.

Another coordinate system is shown in FIG. 3, wherein the horizontal axis designates the compression in kg and the vertical axis designates the distance between the pressure plate 7 and the support platform 5 in cm. The curve 18 in FIG. 3 illustrates the shape which a curve assumes if the pressure plate 7 is flexible and is therefore bent in a defined manner with an increasing compression force exerted against the breast 8. The straight line 19 indicates pressure plate bending. To compensate for bending of the pressure plate 7, the distance established by the distance meter 11 is corrected with a correction value. For example, if the pressure plate is bent by an amount A, the output of the distance meter 11 is corrected with the same value A, and if the pressure plate is bent by an amount B, the output of the distance meter 11 is corrected with the same value B. This results in a curve 20, and the increase in the compression force is stopped, as previously described, when the rate of change of the curve, corresponding to the aforementioned ratio, reaches the predesignated value.

Alternatively, the distance meter 11 can be mounted in the middle of, or close to the free end of, the pressure plate 7, in which case the compensation for pressure plate bending can be eliminated, because it will automatically be taken into account in the output signal in the distance meter 11.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for controlling compression force in an x-ray apparatus for mammographic examinations, comprising the steps of:
    compressing a breast to be examined disposed between a pressure plate and a support platform by increasing a compression force exerted on said breast by moving said pressure plate toward said support platform;
    measuring the thickness of the compressed breast as said compression force is exerted on said breast by said pressure plate; and
    stopping increasing said compression force when a change in the measured breast thickness reaches a preset value.

2. A method as claimed in claim 1 comprising the additional steps of:
    measuring the change in said compression force caused by said pressure plate; and
    stopping increasing said compression force when the change in breast thickness, relative to said change in compression force reaches a further preset value.

3. A method as claimed in claim 2 wherein said further preset value is zero.

4. A method as claimed in claim 1 wherein said preset value is zero.

5. A mammographic examination apparatus comprising:
    means for obtaining a radiographic image of a breast;
    a support platform on which said breast is disposed while obtaining said radiographic image;

a movable pressure plate for compressing said breast between said pressure plate and said support platform with an increasing compression force prior to obtaining said radiographic image and for maintaining said breast compressed while obtaining said radiographic image; and means for controlling said compression force prior to obtaining said radiographic image including means for measuring the distance between said pressure plate and said support platform for generating an output signal corresponding to the thickness of said breast as said compression force increases, and means, supplied with said output signal, for stopping the increase in said compression force when a change in said output signal reaches a preset value.

6. An apparatus as claimed in claim 5 wherein said pressure plate is flexible and is bent in a defined manner as said compression force increases, and further comprising means for correcting said output signal to compensate for bending of said pressure plate.

7. An apparatus as claimed in claim 5 further comprising:

means for measuring said compression force for generating a further output signal; and means for forming a ratio of said output signal and said further output signal and for comparing said ratio to a second predetermined value and for supplying said second predetermined value to said means for stopping, for stopping the increase in said compression force when said ratio reaches said second predetermined value.

8. An apparatus as claimed in claim 7 further comprising a lifting device for said pressure plate, and wherein said means for measuring said distance and said means for measuring said compression force are disposed in said lifting device.

9. An apparatus as claimed in claim 7 wherein said means for calculating said ratio and for comparing said ratio to said second predetermined value comprise a microprocessor.

10. An apparatus as claimed in claim 9 wherein said microporcessor includes means for sampling said output signal and said further output signal.

* * * * *

UNITED STATES PATENT AND TRADEMARK OFFICE
CERTIFICATE OF CORRECTION

PATENT NO. : 5,335,257
DATED : August 2, 1994
INVENTOR(S) : Stefan Thunberg

It is certified that error appears in the above-indentified patent and that said Letters Patent is hereby corrected as shown below:

On title page, item [75],

Correct the spelling of the inventor's name from "Stunberg" to "Thunberg".

Signed and Sealed this

Eighth Day of August, 1995

Attest:

BRUCE LEHMAN

*Attesting Officer*     *Commissioner of Patents and Trademarks*